United States Patent [19]
Shmulewitz

[11] Patent Number: 5,989,263
[45] Date of Patent: Nov. 23, 1999

[54] HYDRAULICALLY ACTUATED DILATATION MECHANISM FOR VESSEL DILATATION AND VASCULAR PROSTHESIS DELIVERY AND METHODS OF USE

[75] Inventor: Ascher Shmulewitz, Mercer Island, Wash.

[73] Assignee: Arteria Medical Science L.L.C., San Francisco, Calif.

[21] Appl. No.: 09/038,798

[22] Filed: Mar. 11, 1998

[51] Int. Cl.[6] .............................. A61F 11/00; A61F 2/06
[52] U.S. Cl. ................. 606/108; 623/1; 606/194
[58] Field of Search .................. 606/108, 192, 606/194, 195, 198; 623/1

[56] References Cited

U.S. PATENT DOCUMENTS

| | | | |
|---|---|---|---|
| 3,557,794 | 1/1971 | Van Patten | 606/198 |
| 3,952,747 | 4/1976 | Kimmell, Jr. | 606/195 |
| 3,996,938 | 12/1976 | Clark, III | 128/348 |
| 4,585,000 | 4/1986 | Hershenson | 128/345 |
| 4,739,762 | 4/1988 | Palmaz | 128/343 |
| 4,998,539 | 3/1991 | Delsanti | 128/898 |
| 5,002,560 | 3/1991 | Machold et al. | 606/198 |
| 5,064,434 | 11/1991 | Haber | 606/198 |
| 5,250,070 | 10/1993 | Parodi | 606/194 |
| 5,354,310 | 10/1994 | Garnic et al. | 606/198 |
| 5,456,667 | 10/1995 | Ham et al. | 604/107 |
| 5,741,270 | 4/1998 | Hansen et al. | 606/108 |

*Primary Examiner*—Todd E. Manahan
*Attorney, Agent, or Firm*—Fish & Neave; Nicola A. Pisano

[57] ABSTRACT

Apparatus having a dilatation mechanism is provided wherein a plurality of radially expanding members are coupled to a plunger. The radially expanding members deflect outwardly in response to application of an hydraulic load to the plunger. The apparatus may be used in dilating vessels to treat obstructive vascular disease, or used in delivery systems to deploy vascular prostheses such as stents and grafts. Methods of using the apparatus are also provided.

30 Claims, 2 Drawing Sheets

HYDRAULICALLY ACTUATED DILATATION MECHANISM FOR VESSEL DILATATION AND VASCULAR PROSTHESIS DELIVERY AND METHODS OF USE

FIELD OF THE INVENTION

The present invention relates to apparatus for treatment of obstructive vascular disease, such as arteriosclerosis, for delivering vascular prostheses. More specifically, the present invention relates to a hydraulically actuated dilatation mechanism suitable for use in restoring patency to constricted body vessels, and for deploying vascular prostheses such as stents and stent-graft systems.

BACKGROUND OF THE INVENTION

Millions of people worldwide are afflicted each year with obstructive vascular disease, such as arteriosclerosis. Conventionally, stenosis of the arteries, such as the coronary arteries, has involved bypass surgery, wherein a synthetic graft or vessel harvested elsewhere in the body is exchanged for the stenosed artery.

In the last twenty years, percutaneous transluminal angioplasty (PTA) has gained wide acceptance as a less traumatic method of treating such disease. In this method, a dilatation device, typically a polyethylene balloon is disposed in the afflicted vessel, such as a coronary artery, and inflated to disrupt the plaque lining the vessel and restore patency to the vessel.

In a large number of cases, to prevent the vessel from later restenosing, a vascular prosthesis "stent") is deployed in the vessel to maintain the patency of the vessel. U.S. Pat. No. 4,739,762 to Palmaz describes one such commercially available stent, which consists of a slotted tubular member. The stent is deployed by plastically deforming the tubular member with a balloon disposed within the interior of the stent.

While use of inflatable balloons in angioplasty and to alleviate other obstructive disease have provided significant benefits to patients, some drawbacks have been recognized for such devices. For example, balloons have been observed to occasionally rupture, and may cause a life-threatening dissection of the vessel. More generally, however, an inflated balloon tends to apply a high compressive load on the endothelial cells lining the vessel. This load may result in damage to the vessel lining, and may even accelerate restenosis. Thus, it would be desirable to provide dilatation apparatus having reduced contact with the vessel lining to preserve more of the endothelium intact.

U.S. Pat. No. 5,250,070 to Parodi recognizes that conventional smooth-walled balloon dilatation devices may lead to extensive damage to the endothelial layer. That patent proposes a dilatation element comprising a series of balloon elements that form ribs when inflated, thus reducing overall contact with the vessel lining compared to smooth-walled balloons. A drawback of the device described in that patent, however, is the complex structure of the balloon member, which renders it impracticable to manufacture.

Another method of reducing contact between the dilatation member and the vessel lining involves constructing the dilatation member with a series of fixed-width bands. For example, U.S. Pat. No. 3,557,794 to Van Patten describes an arterial dilatation element comprising four flexure beams captured between two ferrules. An actuator wire runs to the proximal end of the device, and the flexure beams are made to bow outward by reducing the length of the actuator wire. U.S. Pat. No. 5,354,310 to Garnic et al. and U.S. Pat. No. 5,456,667 to Ham et al., describe devices intended for use as temporary stents to maintain the patency of a vessel for a brief period following dilatation, and which employ a wire mesh and spiral band, respectively, that are actuated by pulling a core member that extends to the proximal end of the devices.

While the dilatation and stenting elements of the aforementioned patents provide reduced contact between the vessel lining and the dilatation element, it is believed that a drawback common to these devices is the inability to transmit sufficient force to the dilatation elements by the actuator wire or core member to effectively disrupt the plaque lining the vessel. In addition, it is believed to develop very high compressive loads with such dilatation elements, the actuator wire or core members may need to be too thick t o readily negotiate tortuous vascular anatomy.

U.S. Pat. No. 4,585,000 to Hershenson describes a screw-operated expanding mandrel enclosed within an elastomeric tube. The screw arrangement in the dilatation element of the Hershenson device may develop the necessary compressive force to disrupt plaque. However, the quadrant-shaped mandrel portions and elastomeric covering employed in that device are expected to provide a compressive force similar to that encountered with smooth-walled balloons.

In view of the foregoing, it would be desirable to provide dilatation mechanisms, and methods of use, that are capable of developing the high compressive forces required to disrupt plaque resulting from obstructive disease, but which have reduced contact with the endothelium compared to smooth-walled balloon dilatation elements.

It further would be desirable to provide dilatation mechanisms and methods suitable for use in deploying vascular prostheses, but which have a lower risk of rupture.

It still further would be desirable to provide dilation mechanisms having reduced contact with the endothelium, compared to smooth-walled balloon dilatation elements, but which have an uncomplicated design and are easy to manufacture.

SUMMARY OF THE INVENTION

In view of the foregoing, it is an object of this invention to provide dilatation mechanisms, and methods, that are capable of developing the high compressive forces required to disrupt plaque resulting from obstructive disease, but which have reduced contact with the endothelium compared to smooth-walled balloon dilatation elements.

It further would be desirable to provide dilatation mechanisms, and methods, suitable for use in deploying vascular prostheses, but which have a lower risk of rupture.

It still further would be desirable to provide dilation mechanisms having reduced contact with the endothelium, compared to smooth-walled balloon dilatation elements, but which have an uncomplicated design and are easy to manufacture.

These and other objects of the invention are accomplished by providing dilatation mechanisms comprising a plurality of radially expanding members coupled to a plunger, so that the radially expanding members deflect outwardly in response to application of an hydraulic load to the plunger. Dilatation mechanisms constructed in accordance with the present invention may be used in dilating vessels to treat obstructive diseases, or used in delivery systems for vascular prostheses.

In preferred embodiments, the dilatation mechanism is mounted on a catheter for transluminal delivery. The plurality of radially expanding members comprise bands having rectangular, oval or circular cross-section, and are mounted between a distally-located endcap and a proximally-located plunger. A core member is coupled to and retains the end cap in a fixed position relative to a distal end of the catheter. The plunger is disposed for translation along the core member responsive to hydraulic pressure applied to the proximal surface of the plunger. The dilatation mechanism is capable of transmitting high radial compressive force to a vessel lining, while preserving a portion of the endothelium.

Methods of using dilatation mechanisms constructed in accordance with the present invention for dilating vessels and deploying vascular prostheses are also provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention provides a dilatation mechanism suitable for use in treating obstructive disease and for deploying vascular prostheses, such as stents and stent-graft systems. Apparatus constructed in accordance with the present invention, when used to treat obstructive vascular disease, is expected to conserve vessel endothelium better than conventional smooth-walled balloon dilatation systems.

Figure 1:
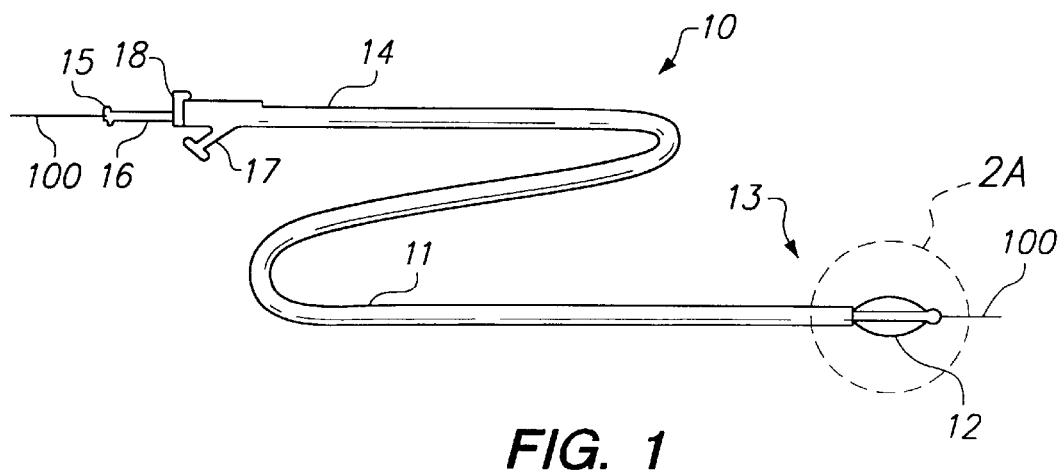
FIG. 1 is a perspective view of an illustrative dilatation system constructed in accordance with present invention.

Referring to FIG. 1, illustrative dilatation system 10 constructed in accordance the present invention is described. Dilatation system 10 comprises catheter 11 having dilatation mechanism 12 disposed from distal end 13 and proximal end 14 having guide wire port 15 extending from core member 16 and luer 17. Core member 16 extends from distal end 13 to proximal end 14 of dilatation system 10, and is fastened in position at proximal end 14 by locking element 18.

Guide wire 100 may be inserted into core member 16 at the distal end of dilatation mechanism 12 and passed through the core member so that the proximal end of the guide wire exits guide wire port 15. This allows dilatation system 10 to be inserted transluminally to a target position in a vessel along guide wire 100, which may be pre-placed in the patient's vessel. Luer 17 is configured to couple to a source of pressurizable medium, such as saline solution contained within a syringe.

Figure 2A:
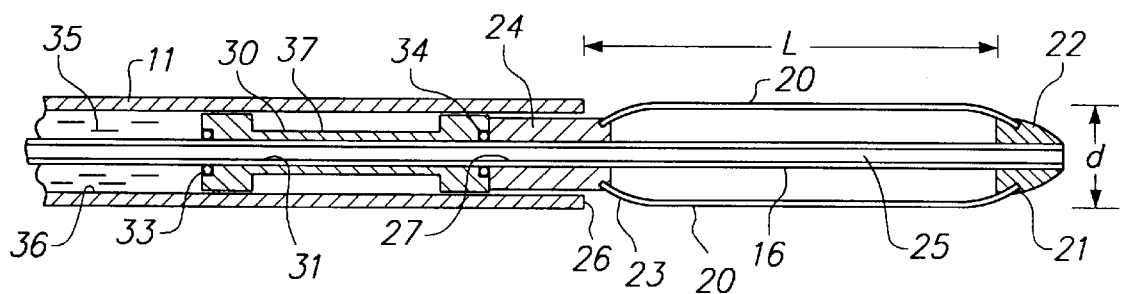
FIGS. 2A and 2B, are respectively, side sectional views of the distal end of the apparatus of FIG. 1 in its transit state and deployed state.
Figure 2B:
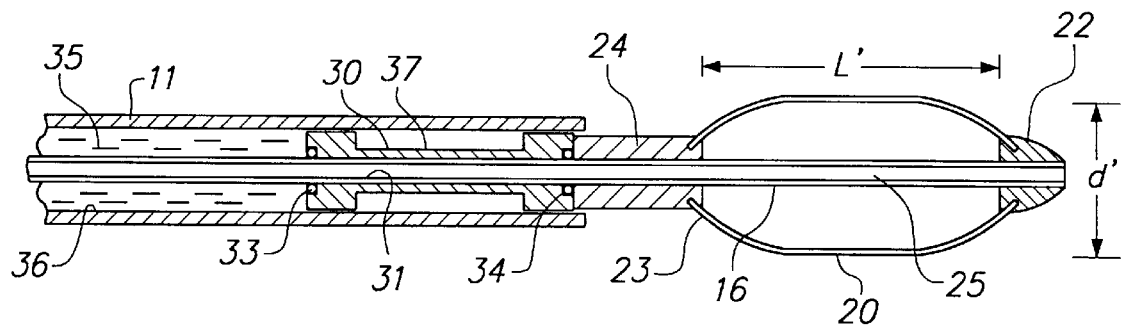
Figure 3:
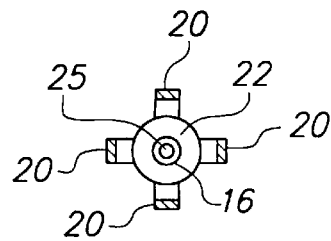
FIG. 3 is an end view taken along view line 3—3 in FIG. 2A.

With respect to FIGS. 2A, 2B and 3, dilatation mechanism 12 comprises a plurality of radially expandable members 20 having distal ends 21 affixed in endcap 22 and proximal ends 23 affixed to push block 24. Radially expandable members 20 may comprise resilient metal alloy or plastic bands and may be fixed to endcap 22 and push block 24 by a biocompatible potting substance, such as epoxy, or with pins. Dilatation mechanism 12 has a collapsed transit position, shown in FIG. 2A, having length L and diameter d, and a deployed state, shown in FIG. 2B, having length L' and diameter d'.

Core member 16 includes lumen 25 and is affixed at its distal end in endcap 22. Core member preferably comprises a high strength, flexible material, such as stainless steel hypotube, or other metal alloy. The proximal end of core member 16 includes a groove 16a in which locking element 18 is engaged see FIG. 5. Accordingly, distal endcap 22 has a fixed position relative to distal end 26 of catheter 11 when locking element 18 is in place. Push block 24 includes bore 27 and is disposed for sliding translation along core member 16. Lumen 25 enables dilatation system 10 to be advanced percutaneously and transluminally along guide wire 100 (see FIG. 1).

Plunger 30 includes bore 31, and is disposed on core member 16 proximally of, and in contact with, push block 24. Plunger 30 includes seals 33 and 34, for example, O-rings, at either end that prevent leakage of pressurizing medium 35 when it is introduced into bore 36 of catheter 11 via luer 17. Plunger 30 preferably has reduced diameter mid-portion 37, which reduces the longitudinal rigidity of the plunger. This feature renders the plunger suitably flexible to negotiate tortuous anatomy.

When a pressurizing medium 35, such as saline solution, is introduced into bore 36 of catheter 11 via luer 17, the medium urges plunger 30 in the distal direction. Plunger 30 in turn abuts against and urges push block 24 towards endcap 22, thereby causing radially expandable members 20 to deflect radially outward. For a predefined volume of pressurizing medium introduced into bore 36, the resulting hydraulic load applied to plunger 30 will cause radially expandable members to undergo a predetermined expansion. Thus, for example, the dimensions of radially expandable members 20 may be selected to provide a predetermined deployed diameter d' and length L', depending upon the size of the stenosis, as determined, for example, by angiography. It is expected that dilatation system 10 may be manufactured having radially expandable members 20 of different lengths, for providing a range of deployed lengths L' and diameters d'.

Catheter 11 preferably comprises a biocompatible material conventionally employed in catheter manufacture, such as polyethylene, polyurethane or nylon, and should be able to withstand internal pressures in bore 36 on the order of 20 to 30 atmospheres. Endcap 22, push block 24 and plunger 30 may comprise similar materials, while sealing rings 33 and 34 preferably comprise an elastomeric material or polytetrafluoroethylene (PTFE). Alternatively, push block 24 and plunger 30 may be replaced by a single element that performs the functions described for those elements hereinabove.

Radially expanding members 20 are preferably spaced equidistant apart around the circumference of dilatation mechanism 12. In FIG. 3, four radially expandable members are depicted. The number of radially expandable members employed will depend upon many factors, including the arc length subtended by each radially expandable member, the transit diameter d and deployed diameter d' of the dilatation system, and the intended application. For example, for use treating obstructive vascular disease, dilatation mechanism preferably employs four to eight members, while a fewer or greater number of radially expandable members may be used for deploying a vascular prosthesis or graft.

Figure 5:
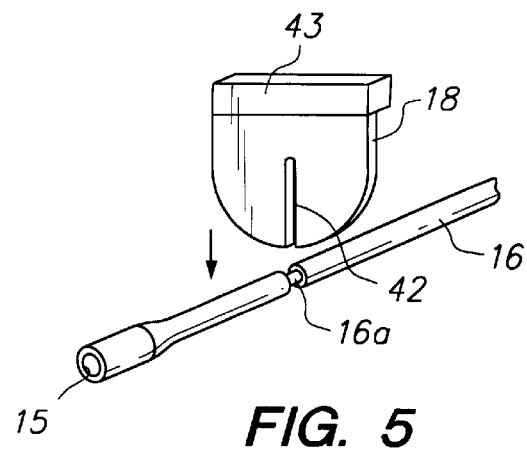
FIG. 5 is a front view of the locking element of FIG. 4.
Figure 4:
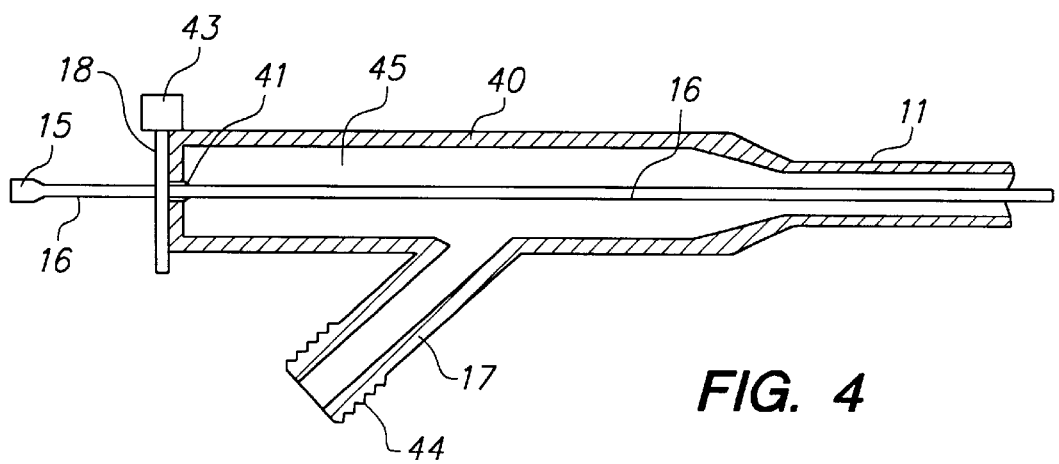
FIG. 4 is a side sectional view of the proximal end of the apparatus of FIG. 1.

With respect to FIGS. 4 and 5, proximal end 14 of dilatation system 10 is described. Proximal end 14 comprises housing 40 coupled to catheter 11, and includes luer 17. Core member 16 extends through seal 41 in housing 40, and terminates in guide wire port 15. Locking element 18, best shown in FIG. 5, includes slot 42 that engages groove 16a in core member 16. When engaged in the groove in core member 16, locking element 18 retains length $L_1$ of core member 16 extending from housing 40. Locking element 18 includes finger grip 43 that permits locking element 18 to be grasped and removed from the groove in core member 16.

Luer 17 may include threads 44 that enable the luer to be coupled to a source of pressurizing medium, preferably a fluid. Housing 40 forms chamber 45 that communicates with bore 36 of catheter 11. Housing 40 preferably comprises a high strength material, such as is commonly used in catheter manufacture. Locking element 18 preferably comprises a machined metal alloy, and may be coated on with a low friction material such as PTFE to reduce frictional forces encountered when the locking element is being removed.

Operation of dilatation apparatus 10 is as follows for use in treating obstructive vascular disease. Once a guide wire is disposed across a stenosis within a vessel, dilatation system 10 is advanced over the guide wire until dilatation mechanism 12 is disposed within the stenosis. A pressurizing medium is then injected through luer fitting 17, causing a hydraulic load to be applied to plunger 30 to translate push block 24 along core member 16. This in turn causes radially expandable members 20 to deflect from the transit position to the deployed position. In the deployed position, radially expandable members 20 apply a tensile force to the plaque forming the stenosis, resulting in disruption of the plaque and restoring the diameter of the flow path within the vessel.

After a predetermined interval of time, locking element 18 may be removed from core member 16. Additional length $L_1$, of core member 16 permits endcap 22 to move distally by an equal amount, thereby enabling radially expandable members 20 to collapse to the transit position. Alternatively, for an embodiment where push block 24 and plunger 30 are either connected or formed as an integral unit, radially expandable members 20 may be restored to the transit position by removing the pressurizing medium from within bore 36 of catheter 11, and or applying suction to the bore to retract plunger 30. In either embodiment, after radially expandable members 20 are returned to the transit position, the dilatation system may be withdrawn from the patient's vessel.

As will be apparent to one of skill in endovascular systems design, the above-mentioned method of operation may also be performed to deploy a vascular prosthesis, such as described in U.S. Pat. No. 4,739,762. Specifically, the stent or graft may be loaded onto the dilatation mechanism prior to transluminal insertion. The dilatation system is then operated as described hereinabove, so that the stent is deployed when the radially expandable members deflect to the deployed state. The dilatation mechanism is then collapsed, and the system withdrawn from the patient, leaving the stent or graft deployed in the patient's vessel.

Figure 6A:
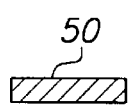
FIGS. 6A, 6B and 6C are, respectively, views of alternative embodiments of the radially expanding elements suitable for use in the present invention.
Figure 6B:
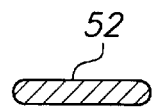
Figure 6C:
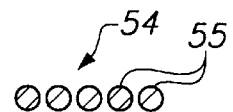

Referring to FIGS. 6A to 6C, several alternative embodiments of radially expandable members 20 suitable for use in the dilatation mechanism of the present invention are described. In FIG. 6A, member 50 is shown having a rectangular cross-section. In FIG. 6B, member 52 has an rounded-rectangular cross-section. In FIG. 6C, each member 54 comprises a plurality of wire elements 55, each wire element 55 having a circular cross-section. Radially expandable members suitable for use in the present invention also may advantageously have other cross-sections, such as oval or elliptical shapes.

Figure 7:
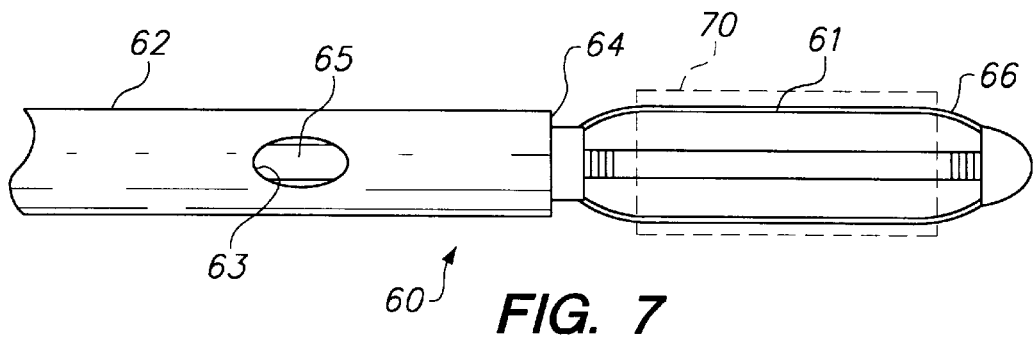
FIG. 7 is a side view of the distal end of an alternative apparatus constructed in accordance with the present invention.

With respect to FIG. 7, an alternative embodiment of the dilatation device of the present invention is described. Dilatation apparatus 60 includes dilatation mechanism 61 which is similar in construction to dilatation system 10 (including dilatation mechanism 12) described hereinabove. Dilatation system 60 differs from the embodiment of FIG. 1 in that catheter 62 includes opening 63 near its distal end 64. Vascular prosthesis 70, such as described in U.S. Pat. No. 4,739,762, is shown in outline disposed on dilatation mechanism 61. opening 63 is positioned so that when plunger 65 (visible through opening 63) is urged to its distal-most position by the pressurizing medium, the proximal face of plunger 65 will pass beyond the proximal edge of opening 63 (compare FIG. 7 to FIG. 2B). When this occurs, the pressurizing medium will pass through opening 63 and into the patient's vessel. In this manner, radially expandable members 66 will attain a maximum deflection corresponding to a maximum distal displacement of plunger 65. Beyond that displacement, excess fluid introduced into catheter 62 will be expelled through opening 63. Accordingly, opening 63 may be designed to provide a maximum upper limit on the radial deflection of expandable members in the deployed state.

The embodiment of FIG. 7 may particularly advantageous for use in deploying vascular prostheses. Vascular prosthesis 70, for example, may comprise a slotted tubular member, as described in U.S. Pat. No. 4,739,762. Vascular prosthesis 70 may be deployed using the methods described in that patent, which is incorporated herein by reference, as modified to employ dilatation apparatus 60 constructed in accordance with the present invention.

The present invention is described hereinabove with respect to illustrative embodiments of a dilatation system designed for over-the-wire use with guide wire 100, i.e., where the guide wire passes through the entire length of the apparatus. The present invention may also be readily adapted for use in a rapid exchange modality, for example, by providing a second lumen in core member 16. That lumen may extend from the endcap of the dilatation mechanism and be brought out through a skive to a lateral surface of the catheter just proximal of the dilatation system.

While preferred illustrative embodiments of the invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. A dilatation system comprising:
    a catheter having a bore and a distal end;
    a plunger disposed within the bore of the catheter; and
    a dilatation mechanism comprising a plurality of radially expandable members, each one of the plurality of radially expandable members having a first end fixed relative to the distal end of the catheter and a second end coupled to the plunger,
    wherein the radially expandable members move between a transit state having an undeflected position, and a deployed state, wherein the radially expandable members are deflected outwards, responsive to application of an hydraulic load to the plunger.

2. The dilatation system as defined in claim 1 wherein the dilatation mechanism further comprises:
   a core member disposed within the bore of the catheter, the core member having a distal end;
   an endcap affixed to the core member, wherein the distal ends of the plurality of radially expandable members are affixed to the endcap.

3. The dilatation system as defined in claim 2 wherein the dilatation mechanism further comprises:
   a push block disposed for sliding translation on the core member distal of the plunger, the proximal end of each one of the plurality of radially expandable members affixed to the push block.

4. The dilatation system as defined in claim 3 wherein the push block is integrally formed with the plunger.

5. The dilatation system as defined in claim 2 wherein a proximal end of the core member has a groove in an exterior surface, and the dilatation system further comprises a locking element that retains the core member in a fixed position relative to the catheter.

6. The dilatation system as defined in claim 5 wherein the locking element is selectively removable to return the radially expandable members to the undeflected transit state.

7. The dilatation system as defined in claim 2 wherein the core member includes a portion defining a guide wire lumen.

8. The dilatation system as defined in claim 7 wherein the core member is configured for over-the-wire use with a guide wire.

9. The dilatation system as defined in claim 1 wherein the catheter further comprises an opening disposed adjacent to the plunger, the opening alleviating the hydraulic load when the radially expandable members attain the deployed state.

10. The dilatation system as defined in claim 1 wherein the plurality of radially expandable members are configured to treat obstructive vascular disease.

11. The dilatation system as defined in claim 1 wherein the plurality of radially expandable members are configured to deploy a vascular prosthesis or graft.

12. The dilatation system as defined in claim 1 wherein radially expandable members comprise an element having a cross-section selected from the group consisting of a rectangle, an oval, and ellipse and a circle.

13. The dilatation system as defined in claim 1 wherein the hydraulic load is imposed by a pressurizing medium introduced into the bore of the catheter.

14. A dilatation system comprising:
    a catheter having a bore and proximal and distal ends;
    a core member having a distal end and a proximal end, the core member disposed within the catheter;
    an endcap disposed on the distal end of the core member;
    a plunger disposed for sliding translation on the core member, the plunger having a proximal end;
    a plurality of radially expandable members, each one of the plurality of radially expandable members having a distal end affixed to the endcap and a proximal end coupled to the plunger,
    wherein the radially expandable members move between a transit state, wherein the radially expandable members are in an undeflected position, and a deployed state, wherein the radially expandable members are deflected outwards, responsive to application of an hydraulic load to the proximal end of the plunger.

15. The dilatation system as defined in claim 14 further comprising a push block disposed for sliding translation on the core member distal of the plunger, the proximal end of each one of the plurality of radially expandable members affixed to the push block.

16. The dilatation system as defined in claim 15 wherein the push block is integrally formed with the plunger.

17. The dilatation system as defined in claim 14 wherein the catheter further comprises an opening disposed adjacent to the plunger, the opening alleviating the hydraulic load when the radially expandable members attain the deployed state.

18. The dilatation system as defined in claim 14 wherein the proximal end of the core member has a groove in an exterior surface, and the dilatation system further comprises a locking element that retains the core member in a fixed position relative to the catheter.

19. The dilatation system as defined in claim 18 wherein the locking element is selectively removable to return the radially expandable members to the undeflected transit state.

20. The dilatation system as defined in claim 14 wherein the plurality of radially expandable members are configured to treat obstructive vascular disease.

21. The dilatation system as defined in claim 14 wherein the plurality of radially expandable members are configured to deploy a vascular prosthesis or graft.

22. The dilatation system as defined in claim 14 wherein the core member includes a portion defining a guide wire lumen.

23. The dilatation system as defined in claim 14 wherein radially expandable members comprise an element having a cross-section selected from the group consisting of a rectangle, an oval, and ellipse and a circle.

24. The dilatation system as defined in claim 14 wherein the hydraulic load is imposed by a pressurizing medium introduced into the bore of the catheter.

25. A method of dilating a vessel to treat obstructive vascular disease, the method comprising:
    providing a dilatation system comprising a catheter, a plunger disposed within the catheter, and a dilatation mechanism comprising a plurality of radially expandable members coupled to the plunger, the radially expandable members movable between a transit state having an undeflected position, and a deployed state, wherein the radially expandable members are deflected outwards, responsive to application of an hydraulic load to the plunger;
    inserting the dilatation system percutaneously and transluminally in a vessel to dispose the plurality of radially expandable members within a stenosis; and
    introducing a pressurizing medium into the catheter to apply an hydraulic load to the plunger that urges the radially expandable members to deflect outwardly to the deployed state.

26. The method as described in claim 25 further comprising:
    after maintaining the radially expandable members in the deployed state for a predetermined interval of time, returning the radially expandable members to the transit state; and
    withdrawing the dilatation system from the vessel.

27. The method as defined in claim 25 wherein providing a dilatation system further comprises:
    selecting a dilatation system including a dilatation mechanism having a length and a diameter, in the deployed state, suitable for treating a stenosis of predetermined size.

28. A method of deploying a vascular prosthesis, the method comprising:

providing a dilatation system comprising a catheter, a plunger disposed within the catheter, and a dilatation mechanism comprising a plurality of radially expandable members coupled to the plunger, the radially expandable members movable between a transit state having an undeflected position, and a deployed state, wherein the radially expandable members are deflected outwards, responsive to application of an hydraulic load to the plunger;

disposing a vascular prosthesis on the dilatation mechanism;

inserting the dilatation system and vascular prosthesis percutaneously and transluminally in a vessel to dispose the vascular prosthesis at a desired location within the vessel; and introducing a pressurizing medium into the catheter to apply an hydraulic load to the plunger that urges the radially expandable members to deflect outwardly to the deployed state to expand the prosthesis into engagement with an interior surface of the vessel.

29. The method as described in claim 28 further comprising:

after maintaining the radially expandable members in the deployed state for a predetermined interval of time, returning the radially expandable members to the transit state; and withdrawing the dilatation system from the vessel.

30. The method as defined in claim 28 wherein providing a dilatation system further comprises:

selecting a dilatation system including a dilatation mechanism having a length and a diameter, in the deployed state, suitable for expanding a vascular prosthesis of predetermined size.

* * * * *